(12) United States Patent
Papalazarou et al.

(10) Patent No.: US 10,492,736 B2
(45) Date of Patent: Dec. 3, 2019

(54) PROVIDING X-RAY IMAGE DATA OF AN OBJECT

(71) Applicant: KONINKLIJKE PHILIPS N.V., Eindhoven (NL)

(72) Inventors: Chrysi Papalazarou, Eindhoven (NL); Gereon Vogtmeier, Aachen (DE); Klaus Juergen Engel, Veldhoven (NL); Herman Stegehuis, Best (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 236 days.

(21) Appl. No.: 15/030,749

(22) PCT Filed: Oct. 30, 2014

(86) PCT No.: PCT/EP2014/073275
§ 371 (c)(1),
(2) Date: Apr. 20, 2016

(87) PCT Pub. No.: WO2015/063191
PCT Pub. Date: May 7, 2015

(65) Prior Publication Data
US 2016/0249869 A1    Sep. 1, 2016

(30) Foreign Application Priority Data

Oct. 31, 2013    (EP) .................................... 13191122

(51) Int. Cl.
*A61B 6/00* (2006.01)
*A61B 6/02* (2006.01)
(Continued)

(52) U.S. Cl.
CPC ............ *A61B 6/027* (2013.01); *A61B 6/0407* (2013.01); *A61B 6/4007* (2013.01);
(Continued)

(58) Field of Classification Search
CPC ........ A61B 6/027; A61B 6/0407; A61B 6/107
See application file for complete search history.

(56) References Cited

U.S. PATENT DOCUMENTS

| 5,852,646 A | 12/1998 | Klotz |
| 6,155,713 A * | 12/2000 | Watanabe ............ A61B 6/4441 378/197 |

(Continued)

FOREIGN PATENT DOCUMENTS

| DE | 102011006122 A1 | 9/2012 |
| DE | 102012202648 B3 | 7/2013 |

(Continued)

*Primary Examiner* — Dani Fox (57) ABSTRACT

A medical imaging system for providing X-ray image data of an object including at least one X-ray detector, an X-ray source arrangement, and a patient configured to receive an object for imaging a region of interest of the object. The at least one X-ray detector is movably mounted above the patient table; and the at least one X-ray detector and the X-ray source arrangement are movable independently. The X-ray source arrangement includes a physical trajectory support structure and is configured to provide X-ray radiation to the region of interest from a number of positions forming a concave open trajectory, wherein a portion of the trajectory and/or the physical trajectory support structure is located below the patient table; and wherein two end regions of the trajectory are extending on the two lateral sides of above the table.

17 Claims, 7 Drawing Sheets

(51) Int. Cl.
*A61B 6/04* (2006.01)
*A61B 6/10* (2006.01)

(52) U.S. Cl.
CPC .......... *A61B 6/4266* (2013.01); *A61B 6/4452* (2013.01); *A61B 6/4458* (2013.01); *A61B 6/4464* (2013.01); *A61B 6/107* (2013.01)

(56) References Cited

U.S. PATENT DOCUMENTS

| | | |
|---|---|---|
| 6,200,024 B1 | 3/2001 | Negrelli |
| 6,325,538 B1 | 12/2001 | Heesch |
| 6,461,039 B1 | 10/2002 | Klotz |
| 7,401,977 B2 | 7/2008 | Graumann |
| 7,938,579 B2 | 5/2011 | Grob |
| 8,335,557 B2 | 12/2012 | Maschke |
| 2008/0240343 A1 | 10/2008 | Jabri |
| 2010/0329534 A1* | 12/2010 | Biermann ............ A61B 6/4441 382/132 |
| 2011/0075814 A1 | 3/2011 | Boese |
| 2012/0241652 A1 | 9/2012 | Jeschke |
| 2012/0250818 A1 | 10/2012 | Helm |

FOREIGN PATENT DOCUMENTS

| | | |
|---|---|---|
| EP | 2596750 A1 | 5/2013 |
| JP | H8275938 A | 10/1996 |
| JP | H1170102 A | 3/1999 |

\* cited by examiner

PROVIDING X-RAY IMAGE DATA OF AN OBJECT

CROSS-REFERENCE TO PRIOR APPLICATIONS

This application is the U.S. National Phase application under 35 U.S.C. § 371 of International Application No. PCT/EP2014/073275, filed on Oct. 30, 2014, which claims the benefit of European Patent Application No. 13191122.4, filed on Oct. 31, 2013. These applications are hereby incorporated by reference herein.

FIELD OF THE INVENTION

The present invention relates to providing X-ray image data of an object, and relates in particular to a medical X-ray imaging system and a method for providing X-ray image data of an object, as well as to a computer program element and to a computer readable medium.

BACKGROUND OF THE INVENTION

In known medical X-ray imaging systems, C-arc systems or U-bracket systems are used, that generally include two separate arm sections, which are connected to one another to form the curved "C" form arm or the U-bracket form arm. When installed or assembled, the X-ray radiation source is arranged on one arm section, and the X-ray radiation detector is arranged on the other arm section. Such a C-arc or U-bracket can also be arranged on an articulated robot arm with six rotation axis, in order to be able to be moved in arbitrary movement paths, and to acquire 3D images of improved 3D imaging quality, or to acquire 3D tomosynthesis images. For interventional or diagnostic procedures, a good image quality of the region of interest of the patient is required; but at the same time, the access to the patient is an important topic. First of all, the necessary space used by the C-arc or U-bracket system next to the patient table is limiting the remaining space available for the doctor and the clinical staff supporting the doctor during the X-ray imaging. It has been shown that with such C-arc or U-bracket systems only a restricted access to the patient may result. Further, some medical X-ray imaging systems comprise a spatially adjustable X-ray source and a spatially adjustable X-ray detector. However, with such C-arc or U-bracket systems arranged on an articulated arm robot with six rotation axis, the risk of collision with the staff, doctor, patient, or patient table, is increased since the trajectories and movements of such systems are less regular, and thus less predictable for the doctor and the staff, than classical C-arc or U-bracket systems. As a consequence, their use requires more concentration or attention from the staff and the doctor, who might risk the system colliding with them if they are not careful enough. Also, more concentration or attention is required from the operator of the system (which could be as well the doctor or a staff member) who could unwillingly control the system so as to collide with the patient or patient table.

However, during interventional or diagnostic procedures, the doctor and his staff should focus their attention to the intervention or to the patient. Moreover, the medical X-ray imaging systems comprising spatially adjustable X-ray source and X-ray detector may not provide an imaging quality similar to the imaging quality of C-arc or U-bracket medical X-ray imaging systems. For example, U.S. Pat. No. 6,461,039 describes a C-arm with a flexible propeller axis rotation.

SUMMARY OF THE INVENTION

Hence, there may be a need to provide a medical X-ray imaging system with reduced space requirements and improved practicability, and that provides X-ray images of imaging quality similar to the ones of C-arc or U-bracket medical X-ray imaging systems.

The object of the present invention is solved by the subject-matter of the independent claims, wherein further embodiments are incorporated in the dependent claims. It should be noted that the following described aspects of the invention apply also for the medical imaging system, and for the method for providing X-ray image data of an object, and for the corresponding computer program element and the computer readable medium.

According to the present invention, a medical X-ray imaging system is provided that comprises at least one X-ray detector, an X-ray source arrangement and a patient table.

The patient table is configured to receive an object for imaging a region of interest of the object. The at least one X-ray detector is movably mounted on a support arm extending from a ceiling. Furthermore, the X-ray source arrangement comprises a physical trajectory support structure extending at least partially below the patient table, Moreover, the X-ray source arrangement is configured to provide X-ray radiation to the region of interest from a number of X-ray source positions defining a concave open trajectory. The physical trajectory support structure is separate from the support arm, that is, the two supports are physically unconnected.

Preferably, the middle portion of the trajectory is located below the patient table, and its two end regions are extending on the two lateral sides of the table and above the table. Furthermore, the plurality of positions, from which the X-ray source arrangement is configured to provide X-ray radiation, is provided by a physical trajectory support structure.

The expression that "positions form a concave trajectory" relates to a number of at least three positions in relation to the region of interest. In a preferred embodiment of the invention, in the case of three positions, a position is located below the patient table, and thus below the region of interest, and two positions are located on respectively each different lateral side of the table, the two positions being furthermore above the table. Those three positions are connected by a trajectory. The two end positions are arranged above the middle portion.

Therefore, the resulting trajectory is concave, or "caved in". Those three positions are thus said to "form a concave trajectory".

In an example, for all points on the concave trajectory, if M1 and M2 are a pair of points of the concave trajectory, the straight line from M1 to M2 is lying above the portion of the trajectory between M1 and M2. In an example, at least two positions are located on respectively each different lateral side of the patient table, above the patient table, and at least one position is located below the patient table.

The term "physical trajectory support structure" relates to a structure that provides the individual positions, from which X-ray radiation is provided, for example a structure with a plurality of (for example at least three) positions in the case of a movable X-ray source, or a structure comprising a plurality of (for example at least three) separate, fixed, X-ray sources. In another example, a combination of one or more movable X-ray sources and one or more fixed X-ray sources is provided as the physical trajectory support structure. Furthermore, in case of a movable X-ray source, the trajectory can also be referred to as a source extension trajectory.

Thus, the X-ray radiation provided from the number of X-ray source positions defining the concave open trajectory, are provided from a movable X-ray source moving via the positions, or from a plurality of separate, fixed, X-ray sources, located at the positions.

The invention is further based on the insight that the combination of an X-ray detector on a ceiling mounted support arm with the plurality of X-ray source positions provides a sufficiently large number of X-ray imaging positions. That is, all imaging positions typically required during an interventional or diagnostic procedure can be achieved using the system according to the invention. Thus, a system is provided having with a relatively simple and compact construction, facilitating access to the patient, without compromise as to the required X-ray imaging functions.

According to an example, the trajectory is provided with an angular coverage of the region of interest of 180 degrees, for example plus fan angle; this means that the X-ray radiations, provided from the number of positions forming the concave open trajectory, are coming from X-ray sources configured to radiate from the number of positions with a corresponding individual fan angle. Each X-ray radiation from each X-ray source with its fan angle creates an X-ray radiation beam. When superimposed, the radiation beams would cover an angle of 180 degrees in the region of interest. The X-ray source fan is predetermined or selectable by the operator of the system, either individually for each X-ray source, or is common to each X-ray source.

According to another example, the patient table is provided with a longitudinal extension direction, and the trajectory is arranged transverse to the longitudinal extension direction.

According to another example, the physical trajectory support structure is movably mounted in relation to the patient table.

According to an example, the trajectory is obtained by two movable arm portions, each having a half-arc geometry.

In an example, the trajectory is obtained by two movable arm portions having a geometry in the form of an half, or less than an half, of the alphabet letter "C", or having a geometry in the form of an half, or less than an half, of a circle.

For example, the movable half-arc arm has a geometry in the form of an half, or less than an half, of the alphabet letter "C" (or in the form of an half, or less than an half, of a circle) and is mounted to a physical trajectory support structure, which can for example be integrated in the patient table support structure, and is located below the table. The physical trajectory support structure supports said movable half-arc arm to move from a first position completely below the table to a second position where one end of the half-arc is extending on one of the lateral sides of the table and above the table, whereas the cantilevering half-arc is still positioned at a position below the table but has moved below the table in a direction towards the side of said one of the lateral sides of the table. It is noted that the term "C" in this context does not mean that detector and source are mounted at opposite ends. Rather, according to the present invention, the detector is mounted such that it can be moved independently.

According to another example, one arm of the two arm portions is placed at an offset position with respect to the other arm position of the two arm portions, the offset positions being measured along the longitudinal extension direction of the patient table.

According to another example, the X-ray source arrangement is provided with at least one movable X-ray source supported movably along a guiding rail following the trajectory.

According to another example, the X-ray source arrangement is provided with a plurality of fixed X-ray sources, distributed along the trajectory at the number of X-ray radiation positions. A combination of, or all of, the X-ray sources can be activated successively or simultaneously with a switching device.

According to another example, an additional X-ray source is provided either below the patient table, or integrated into the patient table, or both.

According to another example, the at least one X-ray detector is mounted to a robotic support arm or to the ceiling on a sliding support. This enables to provide various X-ray detector positions in relation to the patient table and the X-ray source arrangement, as well as enables to place, if adequate for the particular X-ray imaging process, the at least one X-ray detector at a position at a maximum height within the room, thus at a maximum distance from the heads of the clinical staff, thereby reducing collision risks with the heads of the clinical staff.

According to another example, actuators are provided for moving the at least one X-ray detector. Furthermore, a control unit is provided for enabling the at least one X-ray detector to make a corresponding movement in accordance with the change of the X-ray source positions along the trajectory.

According to another example, the X-ray imaging system comprises at least one radiation protection shield, which is movably mounted on the outside of the X-ray source arrangement. The radiation protection shield is movable between a parking position, in which the protection shield is arranged below the table or folded to the side of the X-ray source arrangement, and a protecting position, in which it is provided between the object and a staff member standing next to the patient table, at least in the leg region of the staff member.

According to the present invention, also a method for providing X-ray image data of an object is provided comprising the following steps:
a) arranging an object comprising a region of interest on a patient table;
b) providing successively X-ray radiation to the region of interest by an X-ray source arrangement from a number of positions forming a concave open trajectory;
c) detecting the successive X-ray radiations provided in step b) respectively by at least one X-ray detector mounted movably above the patient table; and
d) generating X-ray image data from the successively detected X-ray radiations.

The middle portion of the trajectory is located below the patient table, and its two end regions are extending on lateral sides of the table and above the table. The number of positions is provided by a physical trajectory support structure;

According to an aspect, besides the main X-ray tube below the patient table, additional X-ray tubes are integrated in a kind of small half C-arc geometry, or—in other words—on additional arms shaped as a half, or less than a half, of the C alphabet letter, or as a half or less than a half, of a circle arc. This last component may be hidden under the table when first quality 3D imaging is sufficient, and thus does not limit the patient access. It is just in case of special 3D imaging request of higher quality than the first quality 3D imaging, that one or two arms move from the position below the patient table to the lateral sides left and/or right from the table. In one example, these arms are equipped with one X-ray tube having one focal spot position, and an X-ray focal beam trajectory is enabled by moving the arm. In combination with at least one moving detector on a robotic arm, a C-arm like projection sequence can be acquired. The same can be done either on one side or both sides of the table. Moreover, instead of a movement of the arm(s) and/or of the detector(s) during the image acquisition, also a switching between several X-ray tubes having fixed focal spot positions is possible. If desired, images can be acquired from different positions along the patient axis, by separating the arm holding the sources into two portions, one to each side of the patient. Each of these portions can be placed independently under the table or lateral to the table, thereby increasing the field of view along the patient axis. Additionally, a flexible radiation shielding having a half-pipe geometry can be mounted on the arm(s) and protects the clinical staff against the X-ray radiation. This flexible radiation shielding can be removed in a very flexible way, and can even be controlled automatically making use of the known geometry of the sources and a model of radiation transport. The invention finds particular application in conjunction with interventional or diagnostic procedures that have heretofore been performed in association with C-arc or U-bracket X-ray imaging systems, or in association with X-ray imaging systems having spaced-apart X-ray source and X-ray detector, and will be described with particular reference thereto.

These and other aspects of the present invention will become apparent from, and be elucidated with reference to, the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
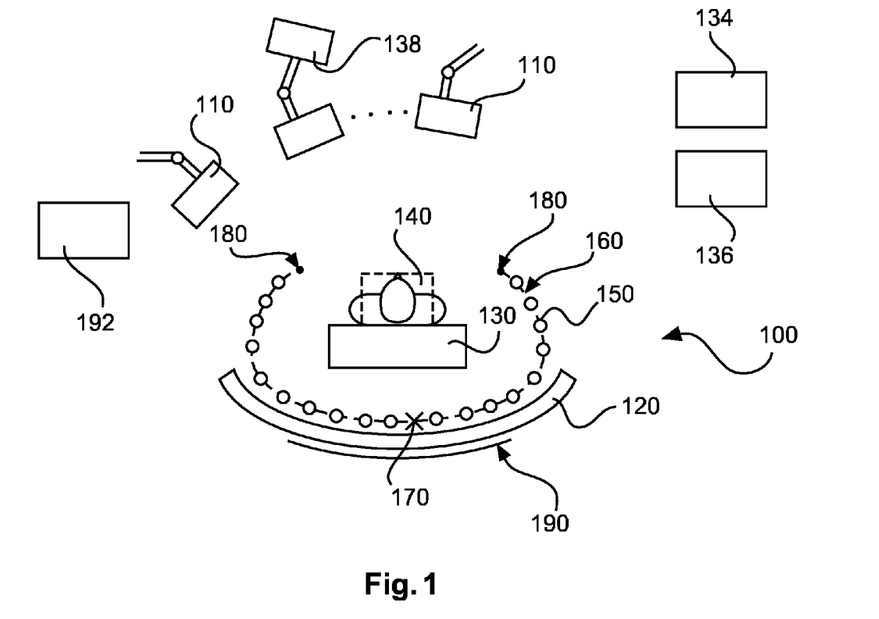
FIG. 1 schematically depicts an example of an imaging system.

A principal sketch of a medical X-ray imaging system 100 according to the present invention is shown in FIG. 1. The system comprises at least one X-ray detector 110, an X-ray source arrangement 120, and a patient table 130. The patient table 130 is configured to receive an object for imaging a region of interest 140 of the object. The at least one X-ray detector 110 is movably mounted on a support arm extending from the ceiling. Generally, the X-ray detector 110 is located above the patient table 130.

Furthermore, the X-ray source arrangement 120 is configured to provide X-ray radiation to the region of interest from a number of positions 150 forming a concave open trajectory 160. As further illustrated in FIG. 1, a middle portion 170 of the trajectory is located below the patient table 130. Two end portions 180 of the trajectory are extending on lateral sides of the table and above the table. The plurality of positions 150, from which X-ray radiation are originating, is provided by a physical trajectory support structure 190 of the X-ray source arrangement 120. In the system illustrated in FIG. 1, the physical trajectory support structure 190 is movably mounted in relation to the patient table 130.

It should be noted that the support arm mounting the at least one X-ray detector 110 and the physical trajectory support structure of the source arrangement 120 are separate and unconnected physical structures being relatively compact, as well as being individually controllable so that the support arm comprising the detector 110 and the source arrangement 120 may move independent from each other. That is, the detector 110 may be moved without simultaneously moving the source arrangement 120, and vice versa.

According to one example, actuators 138 are provided for moving the at least one X-ray detector; a control unit 134 is provided for enabling the at least one X-ray detector to make a corresponding movement in accordance with the change of the X-ray source positions along the trajectory.

According to one example, the patient table 130 is X-ray transparent.

In an example, the concave trajectory is a partly linear trajectory.

In another example, the concave trajectory is virtually connecting a plurality of X-ray radiation sources located at the number of positions. Hence, the trajectory is also referred to as a virtual trajectory.

In an example, the concave trajectory is provided as a part-circular arc. In a further example, the concave trajectory is provided as part-ellipsoidal.

In an example, the system is an interventional X-ray system or a diagnostic X-ray system.

As will be apparent from the description and from the drawings, the geometry of the system is less bulky than the one of a conventional C-arc system or U-bracket system, thereby reducing the risks of collisions with the clinical staff and with the patient. The geometry of the system furthermore improves the workflow for interventional procedures or diagnostic procedures for the following reasons:

The space required for the X-ray medical imaging system according to the present invention is reduced in comparison with a conventional C-arc system or U-bracket system. That is, instead of one relatively bulky C-arm or U-bracket, two relatively compact supports are provided that may be moved independent from each other: a detector support on the ceiling and a source arrangement having a trajectory support structure that is at least partly provided below the patient table.

The trajectory support structure 190 is partly located below the table; preferably, it can further extend above the table more or less, on the left side and/or the right side laterally of the table; this extension above the table of the trajectory, on the left side and/or the right side laterally of the table, will still be less bulky than a conventional C-arc system or U-bracket system; moreover, the X-ray source arrangement will not always occupy the full trajectory, as will be apparent from the following.

During imaging, the equipment around the table can be kept in place as long as it does not conflict with the X-ray source arrangement trajectory or the at least one X-ray detector positions. Since the at least one X-ray detector is provided on a dedicated ceiling support, its movement may be independent from, and uncorrelated to, any movement of the source arrangement. Thus, the doctor and his staff are less in danger of being hit by an element of the X-ray medical imaging system.

In particular, for example, the X-ray source arrangement can be moved in a first step while the X-ray detector is kept in position. Then, in a second step, the at least one X-ray detector is moved while the source arrangement is kept in position. The doctor and his staff can then focus first their attention to the movement of the X-ray source arrangement, and then to the movement of the support arm comprising the at least one X-ray detector, or vice versa.

Furthermore, since the X-ray source arrangement defines a trajectory arranged transverse to the longitudinal extension direction of the patient table, the movement or the positioning of the X-ray source arrangement are predictable by the doctor and the clinical staff. As a consequence, the command of the movements, and the movement itself, of the X-ray source arrangement, requires less concentration or attention from the side of the staff and the doctor, and requires also less concentration or attention from the side of the operator of the system than the concentration or attention required for a C-arc or U-bracket systems arranged on an articulated arm robot with multiple rotation axis.

Moreover, in combination with at least one moving X-ray detector, a C-arm like projection sequence can be acquired, from which a 3D volume can be reconstructed.

In another example, the 3D volume can be reconstructed from a projection sequence acquired by moving the X-ray source arrangement, thereby changing, continuously or discretely, the X-ray source positions, and having a fixed X-ray detector position.

In an example, the system further comprises a projector 192 for projecting high quality images. Alternatively or additionally, the system may comprise glasses, such as "Google-type glasses", to be worn by the clinical staff for individual image projection, or may comprise overlay presentation means for overlay presentation of acquired 3D X-ray images with the real patient body surface.

In one example, the system comprises a control unit 134 for enabling the at least one X-ray detector to follow the movement of the X-ray source arrangement. The control unit 134 provide as well the controls for the movement of the at least one X-ray detector and the independent movement, correlated or uncorrelated to the movement of the at least one X-ray detector, of the X-ray source arrangement.

In one example, the system includes additionally a staff tracking unit 136 which detects the position of the clinical staff and sends this information to the control unit 134 for further processing.

Figure 2:
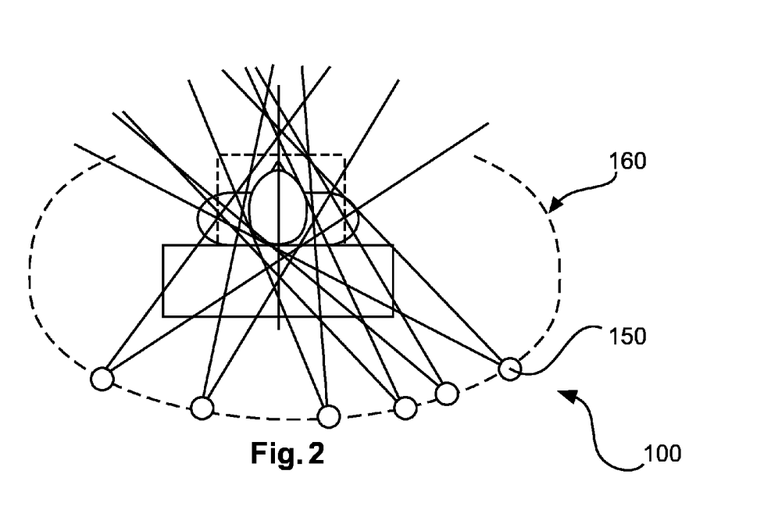
FIG. 2 schematically depicts an angular coverage of a trajectory with regard to a region of interest.

FIG. 2 schematically illustrates that the trajectory is provided with an angular coverage of the region of interest of 180°, plus the fan angles. The X-ray radiations provided from the number of positions forming the concave open trajectory are coming from X-ray sources configured to radiate from the number of positions with a corresponding individual fan angle. Each X-ray radiation from each X-ray source with its fan angle creates an X-ray radiation beam. When superimposed, the radiation beams would cover an angle of 180 degrees plus fan angle in the region of interest. The X-ray source fan is predetermined or selectable by the operator of the system. It can be predetermined or individually selected for each X-ray source. It can be common to all X-ray sources.

Figure 3A:
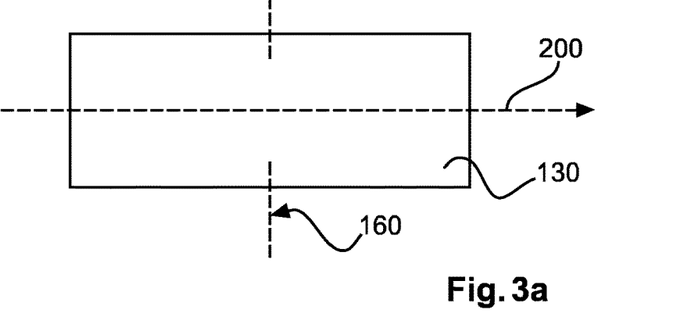
FIG. 3A schematically illustrates a case where the trajectory is arranged transverse to the longitudinal extension direction of the patient table.

FIG. 3A illustrates the system, wherein the patient table 130 is provided with a longitudinal extension direction 200, and wherein the trajectory 160 is arranged transverse to the longitudinal extension direction.

For example, the trajectory is arranged in a plane transverse to the longitudinal extension direction of the patient table.

In an example, the table is movable along its longitudinal extension direction; this enables an imaging of the patient along its longitudinal axis.

Figure 3B:
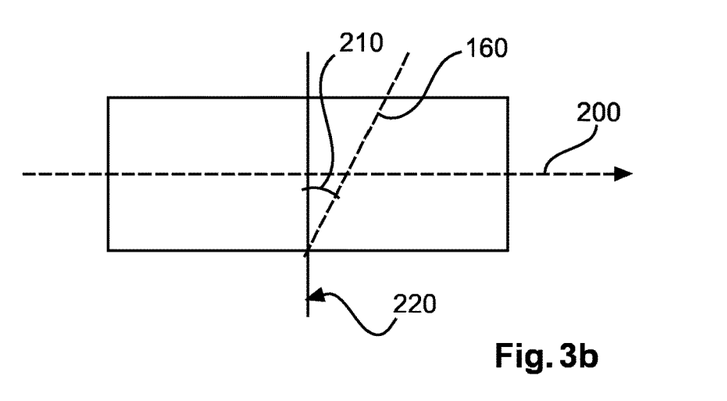
FIG. 3B schematically illustrates a case where the trajectory is arranged to form an angle with the transversal plane of the longitudinal extension direction of the patient table.

FIG. 3B illustrates one example, wherein the concave trajectory is in a direction forming an angle 210 with a transversal plane 220 of the longitudinal extension direction 200.

Figure 4:
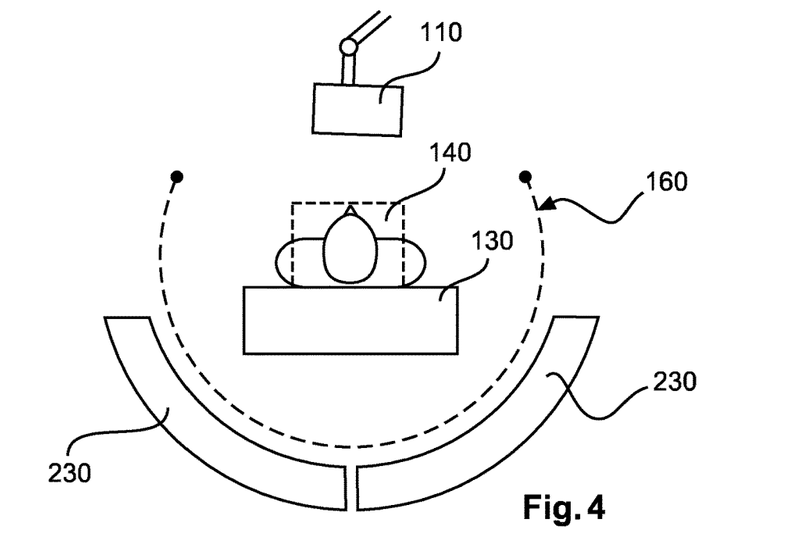
FIG. 4 schematically depicts an example of a trajectory that is obtained by two movable arm portions, each having a half C-arc geometry.

FIG. 4 illustrates a system, in which the trajectory is obtained by two movable arm portions 230, each having a half-C-arc geometry. Another curved-form geometry may be used as well, as long as the resulting trajectory remains a concave open trajectory.

In an example, the two arm portions can be slidably moved below the table; alternatively or additionally, the arm portions are arranged as telescoping arms, which may be extended and contracted accordingly. In another example, the two arm portions are foldable to the side of the patient table, in a plane perpendicular to the table, either following the longitudinal direction of the patient table or following the transversal direction of the patient table.

In an example, when normal 3D imaging quality is needed, the one or two arm portions are slided or contracted under the table or folded to the side of the patient table, which thus does neither limit the patient access, nor obstruct the lateral access to the patient; however, when improved 3D imaging quality or 3D tomosynthesis imaging is needed, the one or two arm portions slide or extend from the below the table position, or from the folded to the side of the table position, to a position on the lateral side of the table, and extending over the table, on the left and/or on the right of the table, thereby providing a physical trajectory support of the concave trajectory.

In an example, each of the two arm portions has a partly linear geometry or multi-linear geometry, under the constraint that the resulting trajectory is a concave open trajectory. In another example, each of the two arm portions is itself constituted by two arms.

In a further example, each of the two arm portions is a grid-like arm, i.e. an arm whereon the X-ray sources are arranged at respective positions on a grid. The one or two arm portions are providing a physical trajectory support structure of the concave trajectory.

Figure 5:
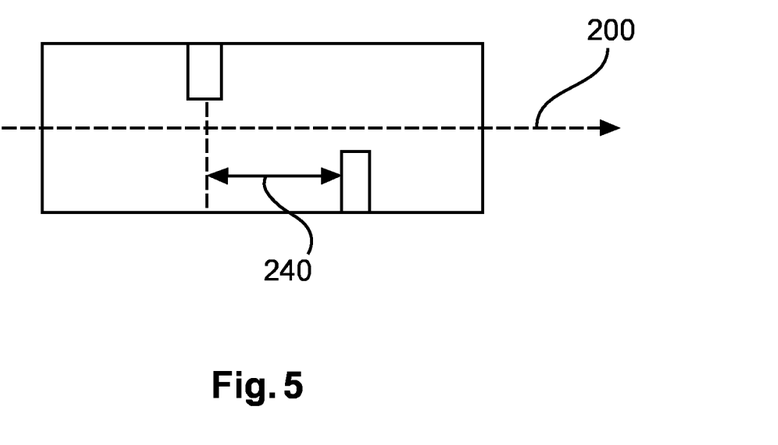
FIG. 5 schematically illustrates a case where one arm of the two arm portions is placed at an offset position, along the longitudinal extension direction of the patient table, with respect to the other arm position of the two arm portions.

FIG. 5 illustrates a system according to the present invention, wherein one arm of the two arm portions is placed at an offset position 240 with respect to the other arm position of the two arm portions, the offset positions being measured along the longitudinal extension direction of the patient table.

First of all, this offset enables a better coverage of the X-ray imaging in the longitudinal extension direction of the patient table. Secondly, this offset prevents a collision of the two arms when they are moved to be slid under the patient table.

Figure 6:
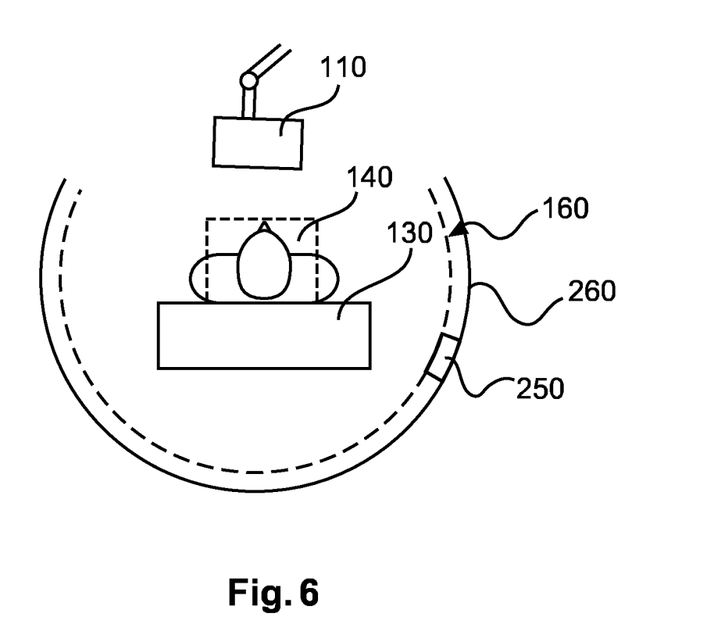
FIG. 6 schematically illustrates an X-ray source arrangement provided with at least one movable X-ray source supported movably along a guiding rail following the trajectory.

FIG. 6 illustrates a system with the X-ray source arrangement being provided with at least one movable X-ray source 250 supported movably along a guiding rail 260 following the trajectory. The term "following" means that the at least one movable X-ray source, when arranged on the guiding rail, can emit X-ray radiation from a number of positions that are lying on the trajectory. The guiding rail provides thus a physical trajectory support of the concave trajectory.

In FIG. 6, the trajectory is represented schematically as part-circular, but it can be part-ellipsoidal as well, or partly linear, concave and open.

Figure 7:
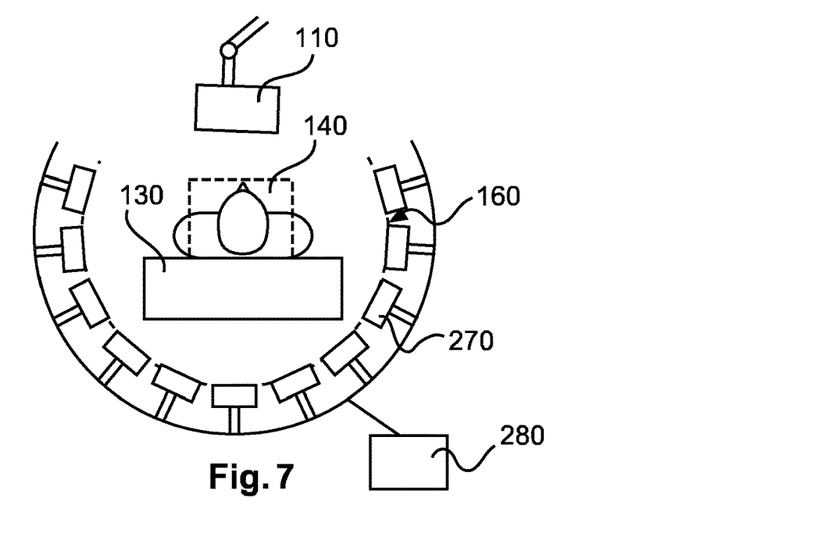
FIG. 7 schematically illustrates an X-ray source arrangement provided with a plurality of fixed X-ray sources distributed along the trajectory at the number of X-ray radiation positions.

FIG. 7 illustrates a system according to the invention, where the X-ray source arrangement is provided with the plurality of fixed X-ray sources 270 distributed along the trajectory at the number of X-ray radiation positions; and some of the X-ray sources can be activated successively or simultaneously with a switching device 280. All of the X-ray sources are activatable.

The plurality of X-ray radiation positions may be regularly or irregularly spaced or located.

In an example, the 3D volume can be reconstructed from a projection sequence acquired by placing the X-ray source arrangement at a fixed position, and switching on or off a combination of, or all of, the X-ray sources of the X-ray source arrangement, thereby activating them or not, and having a fixed X-ray detector position.

In the example, the switching on or off of the X-ray sources of the X-ray source arrangement forms a distributed source array.

In an example, a combination of, or all of, the X-ray sources can be activated successively or simultaneously in sequential or random order.

In an example, the combinations are synchronized. Synchronized double, triple, or a higher multiplicity of, activation combinations are possible.

Figure 8:
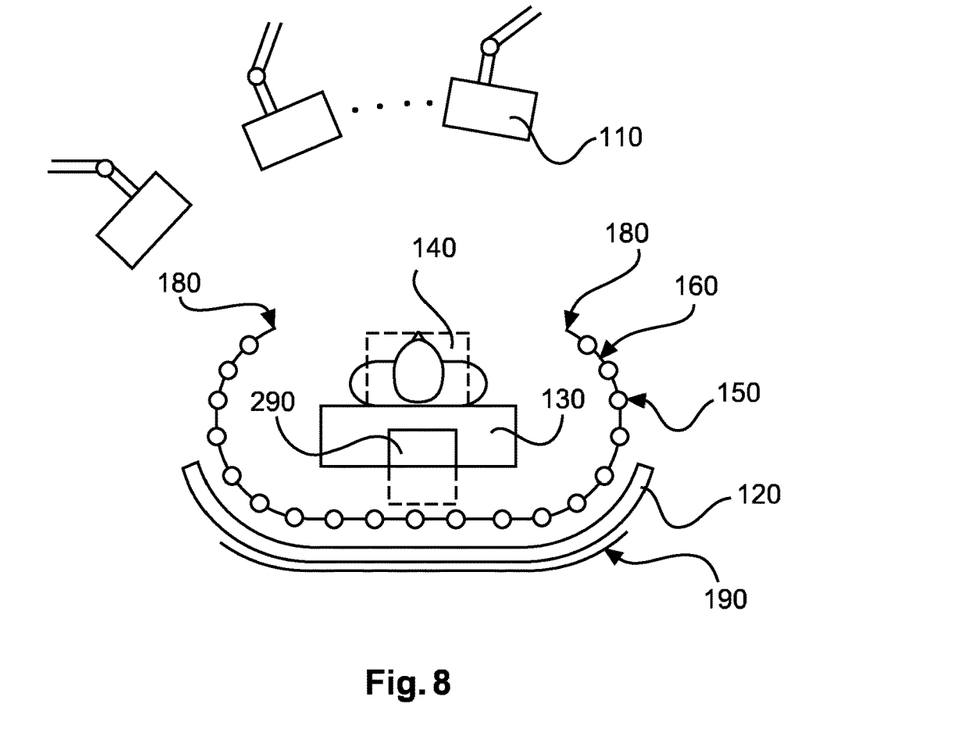
FIG. 8 schematically illustrates an example of a system with an additional X-ray source provided below the patient table and/or integrated into the patient table.

FIG. 8 illustrates an example, where an additional X-ray source 290 is provided in the system of the invention, which additional X-ray source is placed below the patient table, and/or integrated into the patient table. In an example, the additional X-ray source is placed close to the floor or in the floor. Thus it enables to be used in combination with a conventional patient table, without occupying much of the space in the room. In another example, the moveable main X-ray source moves below the table, whereas the movable two arm portions extend the 3D imaging capability and/or allow for tilted projection views without repositioning the patient.

In a further example, a variable beam collimator is located near some or each of the X-ray sources, the operation of which may be synchronized with the at least one X-ray detector movement. Thereby, it reduces the radiation dose by limiting the beam solid angle only towards the actual X-ray detector position.

Figure 9A:
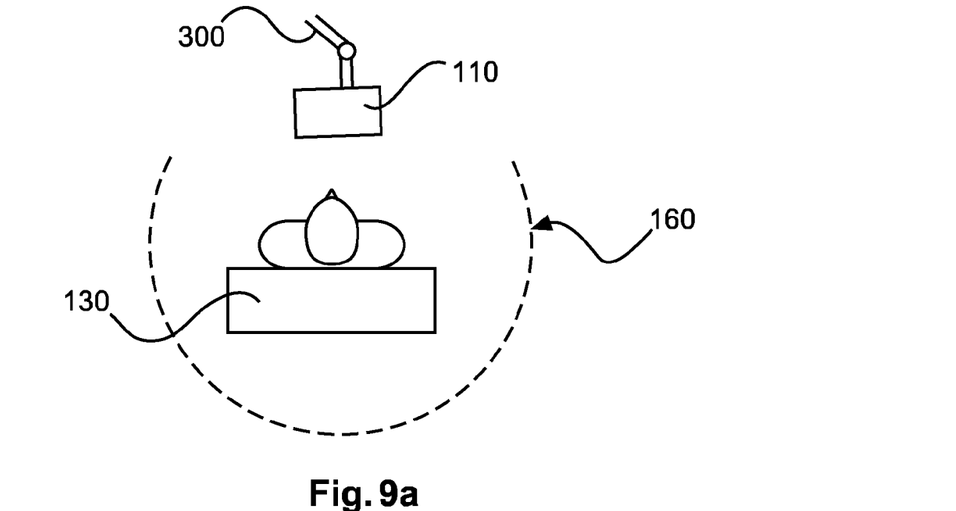
FIG. 9A schematically illustrates an example of a system where the at least one X-ray detector is mounted to a robotic support arm.
Figure 9B:
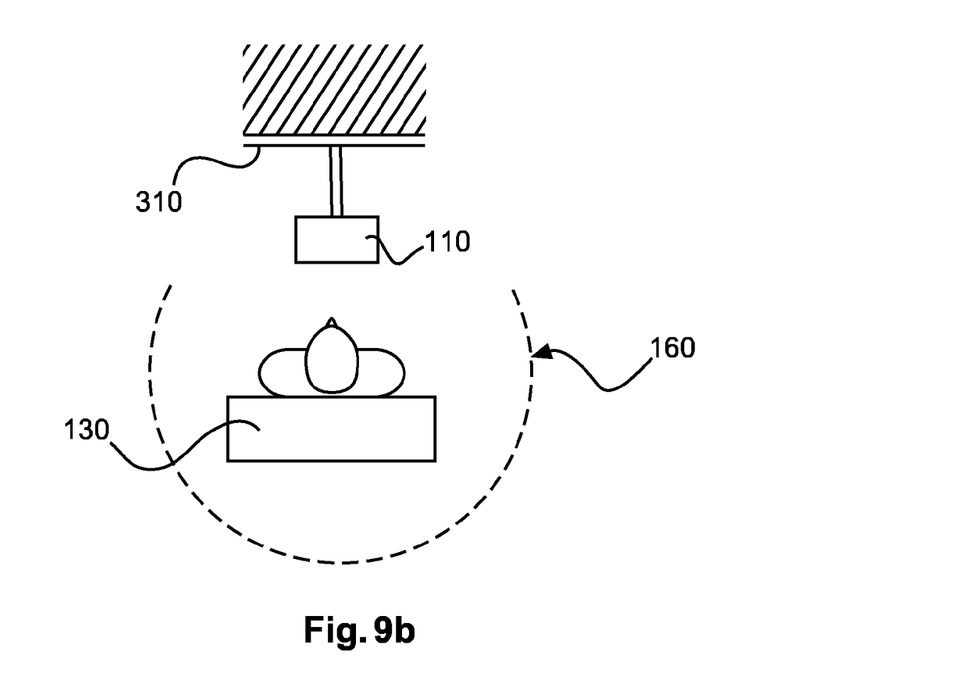
FIG. 9B schematically illustrates a system where the at least one X-ray detector is mounted to the ceiling on a sliding support.

FIG. 9A illustrates a case where at least one X-ray detector is mounted to a robotic support arm 300 extending from a ceiling, whereas FIG. 9B illustrates a simplified embodiment where the at least one X-ray detector is mounted to the ceiling on a fixed, sliding, support arm 310.

In FIGS. 9A and 9B, the trajectory is represented schematically as part-circular, but it can be part-ellipsoidal as well, or partly linear, concave and open.

This arrangement of the at least one X-ray detector on a robotic support arm or on the ceiling on a sliding support enables to provide various detector positions in relation to the patient table and the X-ray source arrangement.

In an example, the at least one detector is mounted on rails at the ceiling.

In an example, two detectors are provided, for example on two separate robotic support arms.

In an example, three, four, or five detectors are provided.

In an example, the at least one X-ray detector can be moved to several positions, including angular tilting, in order to acquire a tomosynthesis-like collection of projection images.

In an example, two detectors on two robotic arms are provided. It enables flexible upgrade packages of the detectors.

The flexibility in the movement from the at least one X-ray detector allows furthermore the adjustment to different magnification factors by selection of the distances between the X-ray detector and the X-ray arrangement.

This system allows as well an optimized region of interest imaging with limited angular view by collimated X-ray beams.

In an example, the system comprises control means 134 for enabling the at least one X-ray detector to follow the movement of the X-ray source arrangement.

In one example, the at least one X-ray detector is a wireless detector or a detector consisting of two or more parallel detectors.

In a further example, the two or more detectors are mounted with an optimized angular alignment such as to obtain computed tomography (CT) "banana", which means that the radiation profiles on the detector are "banana" shaped.

The arrangement of the at least one X-ray detector to a robotic support arm on the ceiling or on a sliding support on the ceiling enables to reduce the risks of collision due to the larger distance of the heads of the clinical staff to the ceiling than to another point above the table in the interventional room.

Figure 10A:
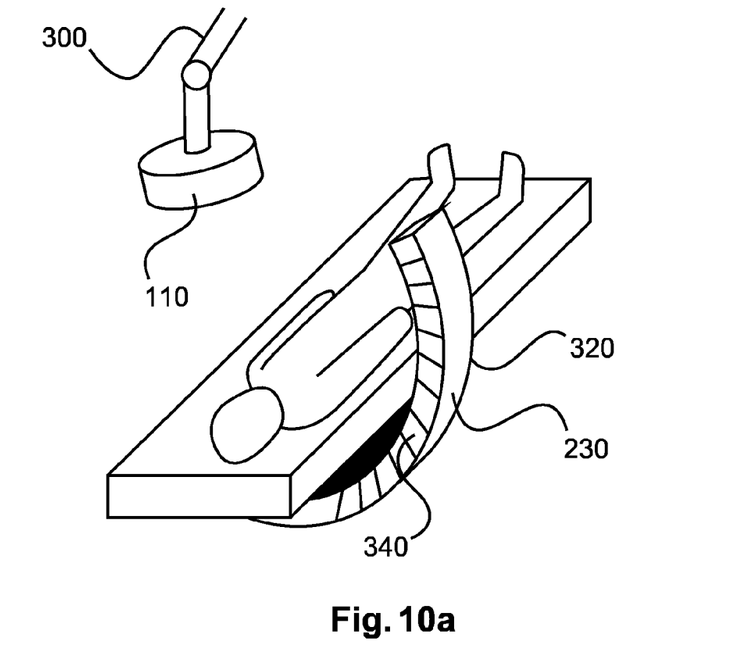
FIG. 10A schematically illustrates a system where the at least one radiation protection shield, movably mounted on the outside of the X-ray source arrangement, is at a parking position.
Figure 10B:
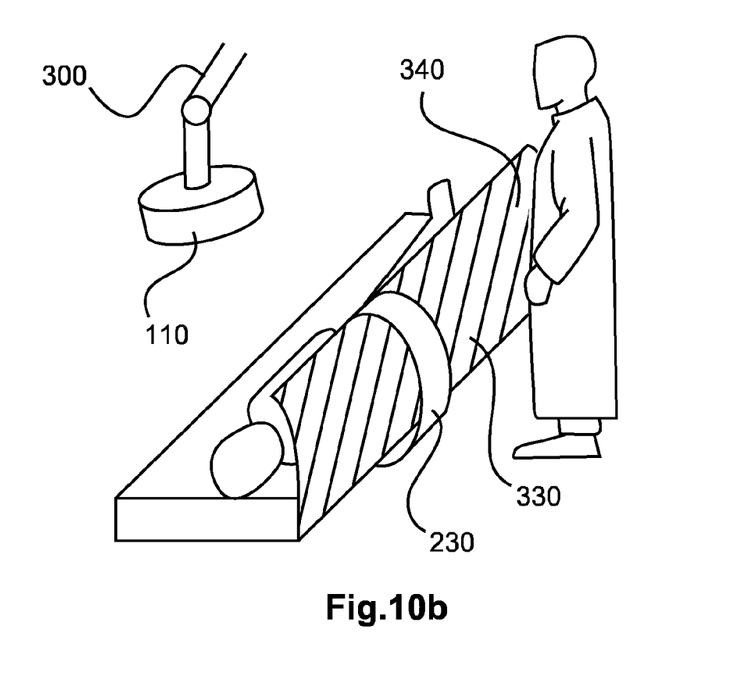
FIG. 10B schematically illustrates a system where at least one radiation protection shield, movably mounted on the outside of the X-ray source arrangement, is at a protecting position.

In FIG. 10A and FIG. 10B, at least one radiation protection shield 340 is illustrated. The at least one radiation protection shield 340 is movably mounted on the outside of the X-ray source arrangement. The radiation protection shield is movable between a parking position 320, in which the protection shield is arranged below the table or folded to the side of the X-ray source arrangement, and a protecting position 330, in which it is provided between the object and a staff member standing next to the patient table, at least in the leg region of the staff member.

This radiation protection shield enables to reduce the exposure of the staff to the X-ray radiations via the inherent geometry of the system.

In one example, the X-ray radiation shielding has a half-pipe geometry.

In another example, the X-ray radiation shielding has a partly linear geometry.

In an example, the geometry of the X-ray radiation shielding is related to the geometry of the arm portion(s): for example, if the arm portion(s) have a half-c arc geometry, the X-ray radiation shielding will have a half-pipe geometry.

In one example, the above-mentioned radiation protection shields are automatically controlled such that they are moved to maximally protect staff from scattered radiation.

In one example, this system includes a modeling unit, which computes an approximation of the scattered radiation for each source position as a model, and a control unit, which uses this calculation of the model to automatically adapt the position of the radiation shield such that scatter is maximally absorbed by the shield. In one example, the position of a moving source is continuously updated and the input fed to the mechanical controller of the shield. In one example, the selected active source from the distributed source array is fed to the mechanical controller of the shield.

In one example, the collimator position is fed to the mechanical controller of the shield.

In another example, this system additionally includes a staff tracking unit, which detects the position of the clinical staff and sends this information to the control unit, which moves accordingly the shield to optimally protect the staff.

The radiation protection shield can be constituted of lamellas of radiation protection materials; for example high-density materials, or low-density material with increased thickness, or for example lead. Other types of radiation protection materials can be used as well.

FIG. 10A illustrates an example when one arm portion is used at the X-ray source arrangement. When there is no X-ray radiation generated, the at least one radiation protection shield is folded to the side of the arm portion. In one example, the radiation protection shield is deployable along the longitudinal axis of the patient table. In another example, the radiation protection shield is deployable along the vertical axis of the patient table.

In one example, the system measures the positions of the X-ray detector and the positions of the X-ray sources and uses this information for calibration and image reconstruction.

Figure 11:
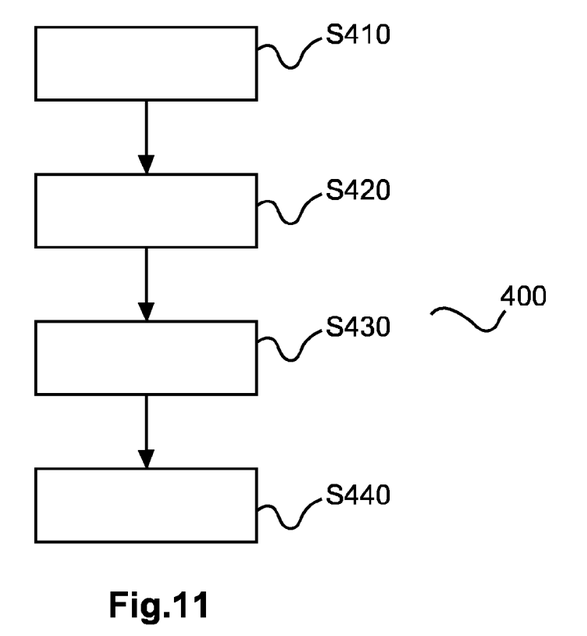
FIG. 11 schematically depicts a method for providing X-ray image data of an object.

FIG. 11 illustrates a method 400 according to the invention for providing X-ray image data of an object, which comprises the following steps:
- a first step S410 of arranging an object comprising a region of interest on a patient table;
- a second step S420 of providing successively X-ray radiation to the region of interest by an X-ray source arrangement from a number of positions forming a concave open trajectory;
- a third step S430 of detecting the successive X-ray radiations provided in the step above respectively by at least one X-ray detector mounted movably above a patient table; and
- a fourth step S440 of generating X-ray image data from the successively detected X-ray radiations.

In the method, the middle portion of the trajectory is located below a patient table; the two end regions of the trajectory are extending on the two lateral sides of the table and above the table; the number of positions are provided by a physical trajectory support structure.

The first step S410 is also referred to as step a), the second step S420 as step b), the third step S430 as step c) and the fourth step S440 as step d).

Figure 12:
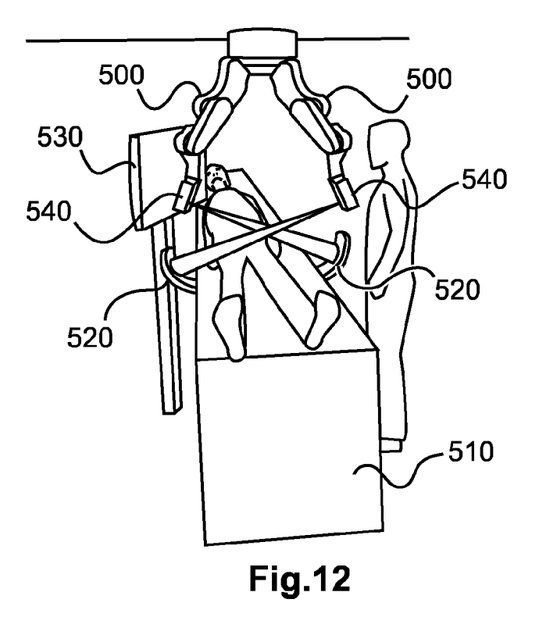
FIG. 12 is an illustration of an example of a medical X-ray imaging system.

FIG. 12 describes a particular configuration of a medical X-ray imaging system of the invention. In FIG. 12, a doctor, a clinical staff, or an operator of the medical X-ray imaging system is standing next to a patient table 510. Two arm portions 520 at each lateral side of the patient table are providing X-ray radiation from a number of positions to a region of interest of the patient. One or a plurality of X-ray radiation is provided from each arm portion at respectively each lateral side of the patient table. The number of X-ray radiations from each arm portion is forming an X-ray beam towards the region of interest of the patient, from each lateral side of the patient table. As an example, the two arm portions represented in FIG. 12 are part-circular, or have a half C-arc geometry. Thus, the sources of the X-ray radiations are lying on a concave trajectory.

Moreover, two detectors 540 are provided: the first detector is mounted on a first robotic arm located at the ceiling, whereas the second detector is mounted on a second robotic arm, distinct from the first robotic arm, and located at the ceiling as well.

The first detector is controlled by the first robotic arm to be located at a position enabling the detection of one of the X-ray beam, coming from one lateral side, whereas the second detector is controlled by the second robotic arm to be located at a position enabling the detection of the other X-ray beam, coming from the other lateral side.

The medical images generated by the medical X-ray imaging system are three-dimensional high quality or tomosynthesis images, since the projection sequences obtained by the configuration of the X-ray source arrangement and the two X-ray detectors are quite similar to projection sequences obtained by a C-arm or U-bracket system. Full coverage of the region of interest is provided particularly if the two X-ray detectors are at two predetermined extreme positions on the left side and on the right side, laterally of the table, as illustrated in FIG. 12.

It is apparent from the figure that the geometry of the system is less bulky than the one of a conventional C-arm or U-bracket system. The 3D medical images are displayed on a screen or a monitor 530. The two arm portions at each lateral side of the patient table can be further equipped with a flexible shielding to protect the clinical staff from the X-ray radiation. This flexible radiation protection shielding can be mounted on each arm portions and deployed along the patient table's longitudinal direction or patient table's longitudinal extension direction, in order to protect the staff against scattered radiations. The deployment of the flexible radiation protection shielding along the patient table's longitudinal direction could be controlled to extend along the table's longitudinal direction in accordance with, or proportionally to, the level and direction of the radiations, or of the scattered radiation. In another example, this flexible radiation protection shielding can be deployed along the vertical direction towards the ceiling, in accordance with, or proportionally to, the level and direction of the radiations, or of the scattered radiation.

When normal quality 3D imaging is sufficient, or when no imaging is performed, the two arm portions can be slid under the table or folded to the side of the table. Then, the clinical staff can freely move around the patient table.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an update turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the Internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject-matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject-matter also any combination between features relating to different subject-matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A medical X-ray imaging system, comprising:
at least one X-ray detector;
an X-ray source arrangement; and
a patient table;
wherein the patient table is configured to receive an object on a top a surface for imaging a region of interest of the object above the top surface;
wherein the at least one X-ray detector is movably mounted on a support arm extending from a ceiling;
wherein the X-ray source arrangement comprises a physical trajectory support structure that extends at least partially below the patient table, the source arrangement being configured to provide X-ray radiation to the region of interest from a number of X-ray source positions being provided by the physical trajectory support structure, wherein at least one of the X-ray source positions provides X-ray radiation to the region of interest after passing through the patient table, the X-ray source positions defining a trajectory having a concave open portion on two opposite lateral sides of the patient table and having a linear portion extending below the patient table towards the two opposite lateral sides,
the physical trajectory support structure being separate from the support arm and including a concave open portion on the two opposite lateral sides of the patient table and having a linear portion extending below the patient table towards the two opposite lateral sides thereby providing the trajectory.

2. System according to claim 1, wherein a middle portion of the physical trajectory support structure includes at least one X-ray source position located below the patient table on the linear portion of the physical trajectory support structure and two end regions of the physical trajectory support structure correspondingly extend on the two opposite lateral sides above the patient table.

3. System according to claim 1, wherein the patient table is provided with a longitudinal extension direction; and
wherein the trajectory is arranged transverse to the longitudinal extension direction.

4. System according to claim 1, wherein the physical trajectory support structure is movably mounted in relation to the patient table and is provided as telescoping arms that extend telescopically to provide the X-ray source positions and that contract to below the patient table.

5. System according to claim 4, wherein the physical trajectory support structure comprises two movable arm portions, each having a half C-arc geometry and a linear geometry extending away from the half C-arc geometry.

6. System according to claim 5, wherein one arm of the two arm portions is placed at an offset position with respect to the other arm position of the two arm portions, the offset positions being measured along the longitudinal extension direction of the patient table.

7. System according to claim 1, wherein the physical trajectory support structure is provided as a guiding rail that is extended along the trajectory and the X-ray source arrangement is provided with at least one moveable X-ray source supported movably directly by and along the guiding rail following the trajectory.

8. System according to claim 1, wherein the physical trajectory support structure is provided as a guiding rail that is extended along the trajectory and the X-ray source arrangement is provided with a plurality of fixed position X-ray sources distributed along the trajectory affixed at the number of X-ray radiation positions; and wherein a combination of, or all of, the X-ray sources are configured to be activated successively or simultaneously, with a switching device.

9. System according to claim 1, wherein an additional X-ray source is provided:
i) below the patient table; and/or
ii) integrated into the patient table.

10. System according to claim 9, wherein the support arm mounting the at least one X-ray detector is a robotic support arm being arranged for providing various X-ray detector positions in relation to the patient table and the X-ray source arrangement.

11. System according to claim 10, wherein actuators are provided for moving the at least one X-ray detector; and wherein a control unit is provided for enabling the at least one X-ray detector to make a corresponding movement in accordance with the change of the X-ray source positions along the trajectory.

12. System according to claim 11, wherein at least one radiation protection shield is movably mounted on an outside of the physical trajectory support structure; and wherein the radiation protection shield is movable between a parking position, in which the entire protection shield is folded along a side of the physical trajectory support structure, and a protecting position, in which the radiation protection shield is extended away from the side of the physical trajectory support structure and is provided between the object and a staff member standing next to the patient table, at least in the leg region of the staff member.

13. A method for providing X-ray image data of an object, comprising acts of:

a) arranging an object comprising a region of interest on a patient table;

b) providing successively X-ray radiation to the region of interest by an X-ray source arrangement from a number of positions forming a trajectory having a concave open portion on two opposite lateral sides of the patient table and having a linear portion extending below the patient table towards the two opposite lateral sides, wherein at least one of the number of positions provides X-ray radiation to the region of interest after passing through the patient table, wherein two end regions of the trajectory are extending on the two opposite lateral sides above the table, and wherein the number of positions are provided by a physical trajectory support structure including a concave open portion on the two opposite lateral sides of the patient table and having a linear portion extending below the patient table towards the two opposite lateral sides thereby providing the trajectory;

c) detecting the successive X-ray radiations provided in step b) respectively by at least one X-ray detector mounted movably above the patient table; and d) generating X-ray image data from the successively detected X-ray radiations.

14. Computer program element for controlling a medical X-ray imaging system according to claim 1, which, when being executed by a processing unit, is adapted to perform acts of:

arranging an object comprising a region of interest on the patient table;

providing successively X-ray radiation to the region of interest by the X-ray source arrangement from the number of positions forming the trajectory;

detecting the successive X-ray radiations provided respectively by the at least one X-ray detector mounted movably above the patient table; and generating X-ray image data from the successively detected X-ray radiations.

15. Non-transitory computer readable medium having stored the program element of claim 14.

16. A medical X-ray imaging system, comprising:
at least one X-ray detector;
an X-ray source arrangement; and
a patient table;
wherein the patient table is configured to receive an object on a top a surface for imaging a region of interest of the object above the top surface;
wherein the at least one X-ray detector is movably mounted on a support arm extending from a ceiling;
wherein the X-ray source arrangement comprises a physical trajectory support structure, the source arrangement being configured to provide X-ray radiation to the region of interest from a number of X-ray source positions being provided by the physical trajectory support structure, the X-ray source positions defining a trajectory having a concave open portion on two opposite lateral sides of the patient table and having a linear portion extending below the patient table towards the two opposite lateral sides with at least one X-ray source position at least partially below the patient table, wherein the at least one of the X-ray source position provides X-ray radiation to the region of interest after passing through the patient table,
the physical trajectory support structure being separate from the support arm and including a concave open portion on the two opposite lateral sides of the patient table and having a linear portion extending below the patient table towards the two opposite lateral sides thereby providing the trajectory.

17. System according to claim 16, wherein a middle portion of the physical trajectory support structure includes at least one X-ray source position located below the patient table on the linear portion of the physical trajectory support structure and two end regions of the physical trajectory support structure correspondingly extend on the two opposite lateral sides above the patient table.

* * * * *